United States Patent [19]

Yoshinaka et al.

[11] 4,399,311

[45] Aug. 16, 1983

[54] PROCESS FOR PRODUCING AROMATIC ALDEHYDES

[75] Inventors: Shigeo Yoshinaka; Tsukasa Toki; Misuzu Wakatsuki; Seiji Uchiyama, all of Niigata, Japan

[73] Assignee: Mitsubishi Gas Chemical Company, Inc., Tokyo, Japan

[21] Appl. No.: 282,733

[22] Filed: Jul. 13, 1981

[30] Foreign Application Priority Data

Jul. 16, 1980 [JP] Japan .................................. 55-97151

[51] Int. Cl.$^3$ ....................... C07C 45/42; C07C 45/43
[52] U.S. Cl. ....................................... 568/437; 423/94
[58] Field of Search ........................... 568/437; 423/94

[56] References Cited

U.S. PATENT DOCUMENTS 4,335,263  6/1982  Minai .................................. 568/437

Primary Examiner—Bernard Helfin
Attorney, Agent, or Firm—Wenderoth, Lind & Ponack

[57] ABSTRACT

In a process for producing aromatic aldehydes by reacting chlorinated methylbenzenes with nitric acid, the improvement wherein a lead compound is added to the residue left after separation and recovery of the resulting aromatic aldehydes from the reaction mixture thereby to remove a chlorine ion present in the residue as a precipitate of lead chloride, and the residue left after removal of the lead chloride is recycled to the reaction of the chlorinated methylbenzenes with nitric acid.

3 Claims, No Drawings

PROCESS FOR PRODUCING AROMATIC ALDEHYDES

This invention relates to a process for producing aromatic aldehydes from chlorinated methylbenzenes.

Aromatic aldehydes typified by benzaldehyde or terephthalaldehyde are useful as intermediate materials for the production of medicines, agricultural chemicals, dyes, polymers and other various industrial chemicals, and find extensive application.

Heretofore, the aromatic aldehydes have been known to be produced by various methods, for example the direct oxidation of methylbenzenes, the hydrolysis of dichloromethylbenzenes, the oxidation of chloromethylbenzenes, and the reduction of chloroformylbenzenes. Recently, the present inventors proposed a method which comprises reacting a mixture of several chlorinated methylbenzenes having different degrees of chlorination with nitric acid to convert the chlorinated methylbenzenes into aromatic aldehydes (U.S. Ser. No. 166,114, and DT-OS No. 3025475).

According to the method of U.S. Ser. No. 116,144 and DT-OS No. 3025475, a mixture of chlorinated methylbenzenes having different degrees of chlorination produced by chlorinating methylbenzenes can be utilized as such as a raw material for aromatic aldehydes. Hence, the raw material is easily available, and the yield of the starting chloride based on methylbenzene can be greatly increased.

However, the above prior art method has the disadvantage that nitric acid in a low concentration must be used in excess for reaction with chlorinated methylbenzenes, and that because the above reaction yields hydrogen chloride, a large amount of a waste liquor containing nitric acid and hydrochloric acid is formed after the desired aromatic aldehydes have been separated from the reaction mixture. Furthermore, when a catalyst is used in the reaction, the waste liquor further contains the catalyst, and therefore requires a troublesome treatment in order to discard it. In addition, this results in discarding of components which can be effectively utilized, and economic losses are inevitable.

It has now been found in accordance with this invention that in the production of aromatic aldehydes by reacting chlorinated methylbenzenes with nitric acid, a chlorine ion in the residue left after the separation of the desired aromatic aldehydes from the reaction mixture can be removed by adding a lead compound to the residue to precipitate it selectively as lead chloride, and that the residue left after separation of the lead chloride can be recycled to the step of reacting the chlorinated methylbenzenes whereby the reaction can be performed without any deleterious effects.

Thus, according to this invention, there is provided, in a process for producing aromatic aldehydes by reacting chlorinated methylbenzenes with nitric acid, the improvement wherein a lead compound is added to the residue left after separation and recovery of the resulting aromatic aldehydes from the reaction mixture thereby to remove a chlorine ion present in the residue as a precipitate of lead chloride, and the residue left after removal of the lead chloride is recycled to the reaction of the chlorinated methylbenzenes with nitric acid.

The process of this invention brings about various advantages. For example, since nitric acid used in excess is recycled to the step of reacting the chlorinated methylbenzenes with nitric acid, an excess of nitric acid is not substantially required. When a catalyst is used in the reaction, it is also recycled to the reaction, and addition of a fresh supply of the catalyst is substantially unnecessary. Furthermore, since the excess of nitric acid or the catalyst contained in the liquid which has heretofore been disposed of as a waste needs not to be discarded, subsidiary materials or a treating operation for the treatment of the waste liquor can be drastically saved, and the process is economically advantageous.

The chlorinated methylbenzenes used as a starting material in the process of this invention denote chlorinated derivatives of xylene or toluene. The xylene derivatives denote one compound of the general formula

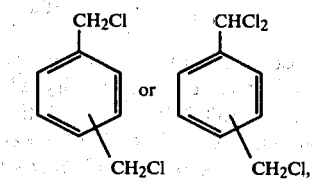

or a mixture of these two compounds, or a mixture of these two compounds with a compound of the general formula

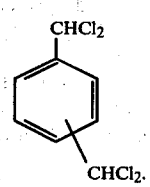

The toluene derivatives denote a compound of the general formula

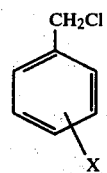

wherein X is H, Cl or Br, or a mixture of it with a compound of the general formula

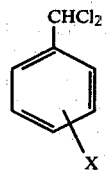

wherein X is H, Cl or Br.

These methylbenzene derivatives may contain minor amounts of other substances.

The aromatic aldehydes denote terephthalaldehyde, isophthalaldehyde or phthalaldehyde when the starting materials are chlorinated xylenes, and benzaldehyde or its halogenated derivatives of the general formula

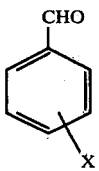

wherein X is H, Cl or Br, when the starting materials are chlorinated toluene derivatives.

The aromatic aldehydes are produced in accordance with the process of this invention by mixing chlorinated methylbenzenes with nitric acid in a predetermined concentration and reacting them at a predetermined temperature with stirring. It is possible to hydrolyze the chlorinated methylbenzenes before the addition of nitric acid and then reacting the hydrolyzed product with nitric acid.

In the practice of the process of the invention, the concentration of nitric acid is generally 0.5 to 15% by weight, preferably 2 to 8% by weight. If the concentration of nitric acid is higher than 15% by weight, formation of by-products carboxylic acids tends to increase. On the other hand, if the concentration of nitric acid is lower than 0.5% by weight, the efficiency of the reaction is reduced and the process is not economically feasible.

The reaction temperature at which the chlorinated methylbenzenes are reacted with nitric acid is generally from 70° C. to 130° C. The preferred reaction temperature is the refluxing temperature of the mixture of the chlorinated methylbenzenes and an aqueous solution of nitric acid being reacted. This temperature is 100° C. or slightly above it. The reaction is usually carried out at atmospheric pressure, but may also be performed under elevated pressures.

The amount of nitric acid is generally 0.2 to 20 moles, preferably 1.0 to 10 moles, per mole of the chlorinated methylbenzenes.

The reaction of the chlorinated methylbenzenes with nitric acid by the process of this invention does not always require a catalyst. The use of a catalyst, however, is preferred because it will shorten the reaction time. Preferred catalysts are vanadium compounds such as vanadium pentoxide, ammonium metavanadate, vanadium chloride, and vanadyl sulfate.

Depending upon the type of the chlorinated methylbenzenes to be reacted, the starting chlorinated methylbenzenes, the reaction intermediates, the desired aldehydes, etc. may deposit as crystals on the reactor wall, or on the cooler during the reaction. Preferably, in order to avoid troubles caused by this deposition, an organic solvent may be added to the reaction system.

Known separating and recovering methods can be used to obtain the desired aromatic aldehydes from the reaction mixture formed by the process of this invention. For example, this can be achieved by a method which comprises cooling the reaction mixture after the reaction and separating the resulting crystals by filtration, a method which comprises separating an oily product which is liberated, or a method which comprises extracting the reaction mixture with an organic solvent.

The resulting aromatic aldehydes contain by-product carboxylic acids which, however, can be removed by washing with dilute aqueous alkali solutions.

The resulting aromatic aldehydes can further be purified usually by distillation, recrystallization, etc.

The above process for producing aromatic aldehydes by the reaction of chlorinated methylbenzenes with nitric acid is described in detail in U.S. Ser. No. 166,114 or DT-OS No. 3025475.

The residue left after separation of the aromatic aldehydes from the reaction mixture by the procedure described above is an aqueous solution containing nitric acid used in excess in the above reaction and hydrogen chloride formed by hydrolysis of the chlorinated methylbenzenes. When a catalyst is used in the reaction, this solution also contains the catalyst used.

According to the process of the invention, a lead compound is added to this aqueous solution to precipitate a chlorine ion in the aqueous solution as lead chloride which is separated by filtration. As a result, hydrogen chloride present in the aqueous solution is selectively removed. This procedure is usually practised at room temperature. Any lead compounds which can perform the above removal of hydrogen chloride can be used in this invention, but those which rapidly dissolve in the aqueous solution to form lead chloride are desirable. From this standpoint, lead nitrate, lead carbonate and lead hydroxide are preferred. Lead carbonate and lead hydroxide are especially preferred in order to recycle lead as mentioned above.

These lead compounds may be added as a solution in water. But in view of the low solubility in water of these compounds and the amount of the residual solution left after removal of lead chloride to be recycled to the reaction of the chlorinated methylbenzenes with nitric acid, these lead compounds are usually added in the form of a solid. The amount of the lead compound is the one sufficient to convert hydrogen chloride present in the residual solution to lead chloride, and can be determined by quantitatively determining the amount of hydrogen chloride.

When the lead compound is added with stirring to the residual solution left after removal of the separation of the aromatic aldehydes, a white precipitate of lead chloride is formed. This precipitate is separated by filtration in a customary manner. The residual solution left after the separation of the precipitate by filtration contains nitric acid, and the catalyst (if used). The residue is recycled to the reaction of the chlorinated methylbenzenes with nitric acid after nitric acid in an amount corresponding to the amount consumed in the reaction with the chlorinated methylbenzenes is supplied and the concentration of nitric acid and the amount of water are adjusted. The reaction with the chlorinated methylbenzenes is carried out in accordance with the conditions described hereinabove, and the reaction mixture after the reaction is treated as described hereinabove.

In the production of aromatic aldehydes by reacting the chlorinated methylbenzenes with nitric acid by the process described hereinabove, the lead compound is added to the residual solution left after separation of the desired aromatic aldehydes from the reaction mixture to remove a chlorine ion in the residue selectively as lead chloride, and while recycling the residual solution left after removal of the lead chloride to the reaction with the chlorinated methylbenzenes, the aromatic aldehydes can be produced from the chlorinated methylbenzenes. Preferably, lead in the separated lead chloride can be recycled as a lead compound for removing hydrogen chloride. This can be achieved by the following procedure.

Specifically, the lead compound is added to the residual solution containing nitric acid, hydrochloric acid, etc. to precipitate lead chloride. The lead chloride is separated by filtration and treated with an aqueous solution of sodium carbonate or sodium hydroxide with stirring to convert it to lead carbonate or lead hydroxide which can then be recycled as the lead compound for removal of hydrogen chloride. The amount of the alkali used in this procedure corresponds substantially to the amount of lead shown by the following scheme.

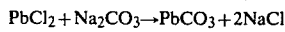

$PbCl_2 + Na_2CO_3 \rightarrow PbCO_3 + 2NaCl$ $PbCl_2 + 2NaOH \rightarrow Pb(OH)_2 + 2NaCl$ Water is required in the above procedure. The amount of water for this purpose may be the one which causes the operation to proceed smoothly. If the amount of water is too small, the above conversion does not take place smoothly. Since in this procedure, the solubility of lead carbonate or lead hydroxide in water is lower than the solubility of lead chloride in water, stirring of a mixture of lead chloride and the aforesaid aqueous alkali solution causes lead chloride to be converted gradually into lead carbonate or lead hydroxide. Some heating is effective in performing this conversion smoothly.

After conversion of lead chloride into lead carbonate or lead hydroxide in this manner, it is separated as a solid by filtration, and the solid can be recycled as the lead compound for removing hydrogen chloride.

According to the process of the invention described above, by recycling the solution containing nitric acid, an excess of nitric acid is not substantially required and the addition of a fresh supply of catalyst is substantially unnecessary. Thus, aromatic aldehydes can be produced in high yields from chlorinated methylbenzenes.

The reaction of the chloromethylbenzenes with nitric acid may sometimes yield a gaseous mixture of $NO_2$ and NO. By adding a small amount of oxygen to the gaseous mixture to change NO to $NO_2$ and performing the reaction while recycling the resulting gaseous mixture to the reaction system, $NO_2$ is absorbed by water to become nitric acid. Thus, the amount of nitric acid can further be reduced, and this provides an advantageous process for producing aromatic aldehydes.

The following examples illustrate the process of this invention without any invention of limiting the invention thereby.

EXAMPLE 1

(A) First Reaction

A 2-liter three-necked flask equipped with a thermometer, a stirrer and a reflux condenser was charged with 84.5 g of a chlorinated p-xylene mixture consisting of 20.7% by weight (17.5 g; 0.1 mole) of $\alpha,\alpha'$-dichloro-p-xylene, 49.7% by weight (42.0 g; 0.2 mole) of $\alpha,\alpha,\alpha'$-trichloro-p-xylene, and 29.6% by weight (25.0 g; 0.10 mole) of $\alpha,\alpha,\alpha',\alpha'$-tetrachloro-p-xylene, 1700 g of 3% by weight nitric acid, 2.5 g of vanadium pentoxide and 3 ml of p-xylene. The mixture was heated with stirring, and reacted under reflux for 9 hours.

After the reaction, the reaction mixture was cooled, and the resulting crystals were separated by filtration. The crystals were then washed with a small amount of a saturated aqueous solution of sodium bicarbonate. As a result of washing, by-product carboxylic acids formed in the reaction moved to the washing. The crystals which remained undissolved during washing were separated by filtration, washed with water, and dried to give 46.9 g of crystals which by infrared adsorption spectroscopy were determined to be terephthaldehyde. The yield of terephthalaldehyde based on the chlorinated xylenes was 87.4%.

The amount of the residual solution which was left after cooling the reaction mixture and separating crystals therefrom by filtration was 1663 g. The concentration of nitric acid in the residual solution was 1.9% by weight, and the concentration of hydrochloric acid formed by the reaction was 2.6% by weight. With stirring, 160 g of a lead carbonate was added to the residual solution, and the mixture was stirred for about 30 minutes. Then, a white precipitate of lead chloride formed was separated by filtration, and washed with a small amount of water. After drying, the amount of the lead chloride was 131.9 g. The concentration of nitric acid in the residual solution left after separation of this precipitate was 1.9% by weight, and the residual solution also contained the vanadium added as the catalyst and about 2% by weight of lead chloride.

To the solution were added 31 g of 61% nitric acid and a small amount of water to adjust its total amount to 1710 g to form a recycle solution for the reaction of the chlorinated xylene mixture.

(B) Second Reaction (the reaction of the recycle solution with the chlorinated xylene mixture)

The same reactor as used in (A) above was charged with 84.5 g of a chlorinated p-xylene mixture having the same composition as in (A) above, 1710 g of the recycle solution obtained by the procedure of (A), and 2 ml of p-xylene. The mixture was heated with stirring, and reacted under reflux for 8 hours.

After the reaction, the reaction mixture was cooled, and the resulting crystals were separated by filtration. The crystals were recrystallized from about 1 liter of water to remove lead chloride included therein, and then worked up in the same way as in (A) above to give 47.0 g of terephthalaldehyde. The yield of terephthalaldehyde based on the chlorinated xylenes was 87.6%.

The amount of the residual solution which was left after separation of the crystals from the reaction mixture by filtration was 1650 g. The concentration of nitric acid in the residual solution was 2.0% by weight, and the concentration of hydrochloric acid in it was 2.6% by weight. To this solution was added 160 g of lead carbonate with stirring, and the mixture was stirred for about 30 minutes. The resulting precipitate was separated by filtration. After drying, the precipitate weighed 161 g. The filtrate resulting from the separation of the precipitate contained 1.9% by weight of nitric acid. To the solution were added 32.1 g of 61% nitric acid and a small amount of water to adjust total amount of the solution to 1710 g to form a recycle solution for use in the reaction of the chlorinated xylene mixture.

(C) Third Reaction

In the same way as in (B) above, 84.5 g of the chlorinated xylene mixture and 1710 g of the recycle solution obtained in (B) above were fed and reacted. The reaction mixture was worked up in the same way as in (A) to give 46.9 g of terephthalaldehyde. The yield of the terephthalaldehyde based on the chlorinated xylenes was 87.4%.

EXAMPLE 2

(A) The same reactor as used in Example 1 was charged with 84.5 g of a chlorinated xylene mixture consisting of 20.7% by weight (17.5 g; 0.1 mole) of α,α'-dichloro-m-xylene, 49.7% by weight (42.0 g; 0.2 mole) of α,α,α'-trichloro-m-xylene and 29.6% by weight (25.0 g; 0.10 mole) of α,α,α',α'-tetrachloro-m-xylene, 1700 g of 3% by weight nitric acid, 3.0 g of ammonium metavanadate, and 3 ml of m-xylene. The mixture was heated with stirring, and reacted under reflux for 8 hours. After the reaction, the reaction mixture was cooled, and the resulting crystals were collected by filtration. The amount of the residual solution was 1660 g. The crystals were worked up in the same way as in Example 1 to give 45.7 g of isophthalaldehyde.

The residual solution contained 2.6% by weight of hydrochloric acid and 1.9% by weight of nitric acod. To the solution was added 142.9 g of lead hydroxide having a lead content of 87% by weight, and the mixture was stirred for about 30 minutes. The resulting white precipitate of lead chloride was separated by filtration. After drying, the amount of the separated precipitate was 132 g.

The residual solution left after the separation of the precipitate contained 1.9% by weight of nitric acid and vanadium added as the catalyst, etc. were present. To the solution were added 31 g of 61% nitric acid and a small amount of water to adjust the total amount of the solution to 1700 g to form a recycle solution for use in the reaction of the chlorinated xylene mixture.

(B) The same reactor as used in (A) above was charged with 84.5 g of a chlorinated m-xylene mixture having the same composition as in (A) above, 1710 g of the recycle solution obtained in (A) above, and 3 ml of m-xylene.

The mixture was heated with stirring, and reacted under reflux for 8 hours. After the reaction, the reaction mixture was cooled, and the resulting crystals were separated by filtration. The crystals were treated in the same way as in Example 1, (B) to give 45.2 g of isophthalaldehyde. The yield of isophthalaldehyde based on the chlorinated m-xylenes was 84.2%.

EXAMPLE 3

(A) The same reactor as used in Example 1 was charged with 61.6 g of a mixture of 44.0% by weight (27.1 g; 0.214 mole) of benzyl chloride and 56.0% by weight (34.5 g; 0.214 mole) of benzal chloride, 1440 g of 3% by weight nitric acid and 2.0 g of vanadium pentoxide. The mixture was heated with stirring, and reacted under reflux for 6 hours.

After the reaction, the reaction mixture was cooled. The liberated oily portion was separated, and washed with a dilute alkali solution to give 39.0 g of an oil. By infrared absorption spectroscopy, the oil was determined to be benzaldehyde. The yield of benzaldehyde based on the chlorides charged was 85.9%.

The amount of the residual solution left after the separation of the oily portion was 1430 g, and the solution contained 1.7% by weight nitric acid and 1.63% by weight of hydrochloric acid. With stirring, 85.8 g of lead carbonate was added, and the mixture was stirred for about 30 minutes. The resulting precipitate of lead chloride was separated by filtration. After drying, the separated lead chloride weighed 59.8 g. The residual solution left after the separation of the precipitate contained 1.7% by weight of nitric acid and a small amount of vanadium dissolved therein.

To the residual solution were added 27.0 g of nitric having a specific gravity of 1.42 and a small amount of water to adjust the total amount of the solution to 1470 g to form a recycle solution for use in the reaction of the chlorinated toluene mixture.

(B) The same reactor as used in (A) above was charged with 61.6 g of a chlorinated toluene mixture having the same composition as in (A) above and 1480 g of the recycle solution obtained in (A).

The mixture was heated with stirring, and reacted under reflux for 6 hours. After the reaction, the reaction mixture was cooled to separate the oily portion. The oily portion was washed with dilute alkali to form an oil weighing 40.2 g. By gas chromatographic analysis, this product was determined to be benzaldehyde. The yield of benzaldehyde was 88.5%.

EXAMPLE 4

(A) A 500 ml photoreaction apparatus equipped with a thermometer, a stirrer, a chlorine blowing tube, a reflux condenser serving concurrently as a gas exhausting device and a light irradiating device including a high-pressure mercury lamp was charged with 318 g (3.0 moles) of p-xylene, and the contents were heated to 130° C. Dry chlorine was blown at a rate of 1.5 moles/hour into the reaction apparatus with stirring under light irradiation. When 9.0 moles in total of chlorine was blown in this condition, the blowing of chlorine was stopped. Then, dry nitrogen gas was passed through the reaction mixture to remove hydrogen chloride and chlorine gas from the reaction system. In this way, 623 g of the reaction solution was obtained.

Gas chromatographic analysis showed that the reaction solution consisted of 0.6 mole % of α-chloro-p-xylene, 1.3 mole % of α,α-dichloro-p-xylene, 22.5 mole % of α,α'-dichloro-p-xylene, 52.9 mole % of α,α,α'-trichloro-p-xylene, 18.7 mole % of α,α,α',α'-tetrachloro-p-xylene, 1.5 mole % of α,α,α,α'-tetrachloro-p-xylene, 1.8 mole % of α,α,α, α',α'-pentachloro-p-xylene and 0.7 mole % of other compounds.

(B) The same reactor as used in Example 1 was charged with 84 g of the chlorinated p-xylene mixture obtained in (A) above, 1700 g of 3% by weight nitric acid, 2.5 g of vanadium pentoxide and 3 ml of toluene. The mixture was heated, and reacted under reflux for 9 hours.

After the reaction, the reaction mixture was cooled, and the crystals were separated by filtration. The resulting crystals were washed with a small amount of a saturated aqueous solution of sodium bicarbonate. As a result of washing, the by-product carboxylic acids formed in the reaction moved to the washing. The crystals which remained undissolved during washing were separated by filtration, washed with water, and dried to give 45.4 g of crystals. The crystals were distilled under a reduced pressure of 15 mmHg to give 44.0 g of a distillate. By infrared absorption spectroscopy, this distillate was determined to be terephthalaldehyde. By gas chromatographic analysis, the terephthalaldehyde was found to have a purity of 99.4%. The yield of the terephthalaldehyde based on the starting p-xylene was 81%.

The reaction mixture was cooled, and the crystals were separated by filtration. The filtrate weighed 1658 g. The concentration of nitric acid in it was 1.9% by weight, and the concentration of hydrochloric acid formed as a result of the reaction was 2.6% by weight. To the filtrate was added 141.4 g of lead hydroxide having a lead content of 87% by weight, and the mixture was stirred for about 30 minutes. The resulting white precipitate was separated by filtration. After drying, the precipitate (PbCl$_2$) weighed 131 g. The residual solution after separation of the precipitate contained 1.9% by weight of nitric acid. To the solution were added 32 g of 61% nitric acid and a small amount of water to adjust the total amount of the solution to 1710 g to form a recycle solution for use in the reaction of the chlorinated xylene mixture.

(C) The same reactor as used in (B) above was charged with 84 g of the chlorinated p-xylene mixture obtained in (A) above, 1710 g of the recycle solution obtained in (B) above, 3 ml of toluene. The mixture was heated and reacted under reflux for 8 hours.

After the reaction, the reaction mixture was cooled, and the resulting crystals were separated by filtration. The crystals separated were recrystallized with about 1 liter of water to remove lead chloride included in it, worked up in the same way as in (B) above and then distilled to give 43.4 g of terephthalaldehyde. The yield of terephthalaldehyde based on p-xylene was 80.0%.

Referential Example 1

1206 g of a 8.8% by weight aqueous solution of sodium carbonate was heated, and with stirring 278 g of lead chloride was added. Stirring was continued for about 30 minutes. Then, the mixture was cooled to form a white precipitate which was separated by filtration. The precipitate was washed with a small amount of water, and dried to give 265.7 g of lead carbonate.

Referential Example 2

1180 g of a 6.8% by weight aqueous solution of sodium hydroxide was heated to 50° C., and with stirring, 278 g of lead chloride was added. Stirring was continued for about 30 minutes. Then, the mixture was cooled, and the resulting precipitate was separated by filtration. A small amount of hydrochloric acid was added to the filtrate to adjust the pH of the filtrate to 10.1, whereupon a small amount of a white precipitate formed again. The precipitate was separated by filtration, and combined with the first-mentioned precipitate. The mixture was washed with a small amount of water, and dried. In this manner, 238 g of lead hydroxide containing 87% by weight of lead was obtained. The threoretical content of lead in lead hydroxide is 85.9% by weight. The higher lead content in the lead hydroxide obtained in this example was due probably to partial dehydration during handling.

What we claim is:

1. In a process for producing aromatic aldehydes by reacting chlorinated methylbenzenes with nitric acid, the improvement wherein a lead compound selected from the group consisting of lead nitrate, lead carbonate or lead hydroxide is added to the residue left after separation and recovery of the resulting aromatic aldehydes from the reaction mixture, thereby to remove a chlorine ion present in the residue as a precipitate of lead chloride, and the residue left after removal of the lead chloride is recycled to the reaction of the chlorinated methylbenzenes with nitric acid.

2. The process of claim 1 wherein the lead compound is added as a solid to the residue.

3. The process of claim 1 wherein the lead chloride removed is treated with an aqueous solution of sodium carbonate or sodium hydroxide to convert it to lead carbonate or lead hydroxide which is re-used in forming a precipitate of lead chloride.

* * * * *